United States Patent [19]
Coffey et al.

[11] Patent Number: 6,162,198
[45] Date of Patent: Dec. 19, 2000

[54] INJECTION SHIELD AND METHOD FOR DISCHARGING A SYRINGE CONTAINING RADIOACTIVE MATERIAL

[75] Inventors: Jack L. Coffey, Camarillo; Steven G. Hauser, Westlake Village; Bing Bing Zhu, Northridge, all of Calif.

[73] Assignee: Syncor International Corporation, Woodland Hills, Calif.

[21] Appl. No.: 08/873,198

[22] Filed: Jun. 11, 1997

Related U.S. Application Data

[60] Provisional application No. 60/019,569, Jun. 11, 1996.

[51] Int. Cl.[7] ........................ A61M 5/325; A61M 5/00; G21C 11/00; G21F 5/00
[52] U.S. Cl. ........................ 604/198; 604/187; 604/192; 604/197; 604/272; 604/263; 250/515.1; 250/506.1
[58] Field of Search ........................ 604/110, 181–82, 604/187–88, 192, 197–199, 218, 263–64, 268, 272; 588/1, 16, 20; 250/505.1, 506.1, 515.1

[56] References Cited

U.S. PATENT DOCUMENTS

| | | |
|---|---|---|
| 3,294,231 | 12/1966 | Vanderbeck . |
| 3,596,659 | 8/1971 | Glasser ........................ 604/187 |
| 3,973,554 | 8/1976 | Tipton ........................ 250/506.1 |
| 4,060,073 | 11/1977 | Collica et al. ........................ 250/506.1 |
| 4,062,353 | 12/1977 | Foster et al. . |
| 4,122,836 | 10/1978 | Burnett . |
| 5,519,931 | 5/1996 | Reich . |
| 5,527,296 | 6/1996 | Kashanchi ........................ 604/263 |
| 5,536,945 | 7/1996 | Reich ........................ 250/507.1 |
| 5,611,429 | 3/1997 | Phillips ........................ 206/365 |
| 5,743,887 | 4/1998 | Brattesani ........................ 604/192 |
| 5,828,073 | 10/1998 | Zhu et al. . |
| 5,927,351 | 7/1999 | Zhu et al. . |

OTHER PUBLICATIONS

Advertisement for "Syringe Shields", no date but could predate filing date.
Advertisement for "Pro–Tee III Syringe Shield", no date but could predate filing date.
Advertisement for "Pro–Tee II Syringe Shield", no date but could predate filing date.
Advertisement for "Pro–Ect B Syringe Shield", no date but could predate filing date.
Advertisement for "Pro–Tee Syringe Shield", no date but could predate filing date.
The solution to a Broken Syringe is as easy as A, B, C, Journal of Nuclear Medicine, May, 1996.

*Primary Examiner*—Angela D. Sykes
*Assistant Examiner*—Patricia Bianco
*Attorney, Agent, or Firm*—Sheppard, Mullin, Richter & Hampton LLP

[57] ABSTRACT

A shielding device and method for injecting a patient with radioactive material from a syringe to reduce exposure of workers to the radioactive material in the syringe. After the injection, the syringe needle falls away from the shield, thereby minimizing the risk of contamination of the shield from the contaminated syringe needle.

29 Claims, 9 Drawing Sheets

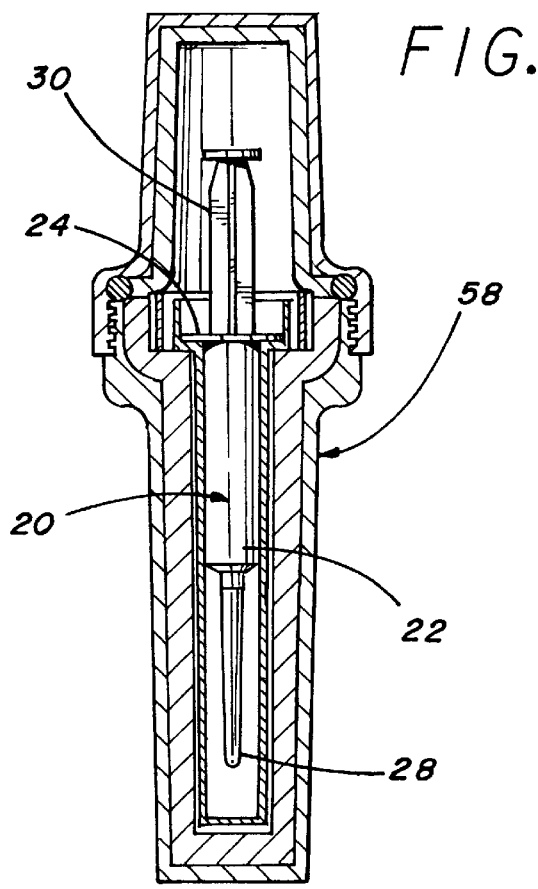
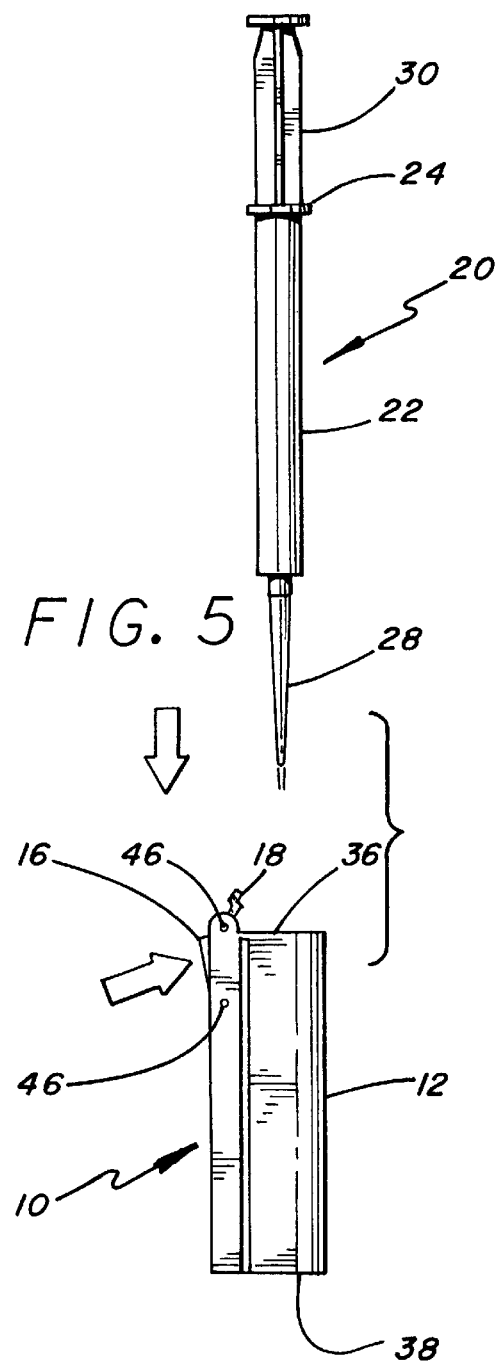
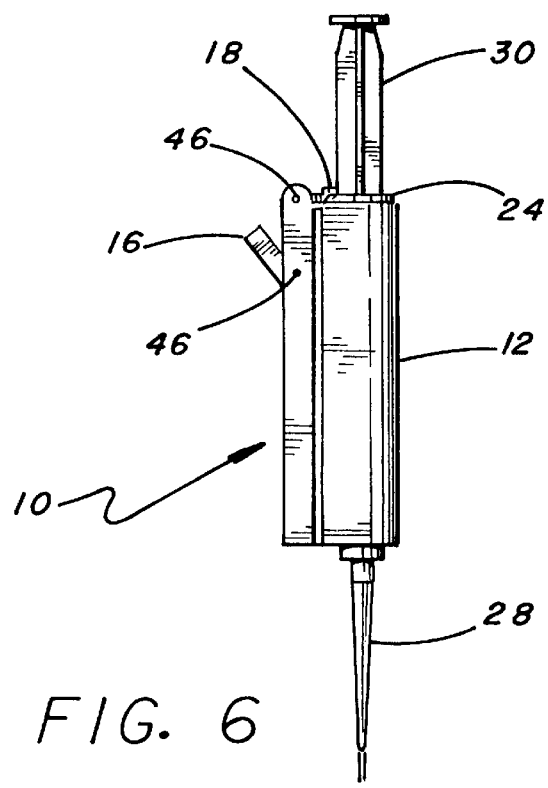
FIG. 4
FIG. 5
FIG. 6

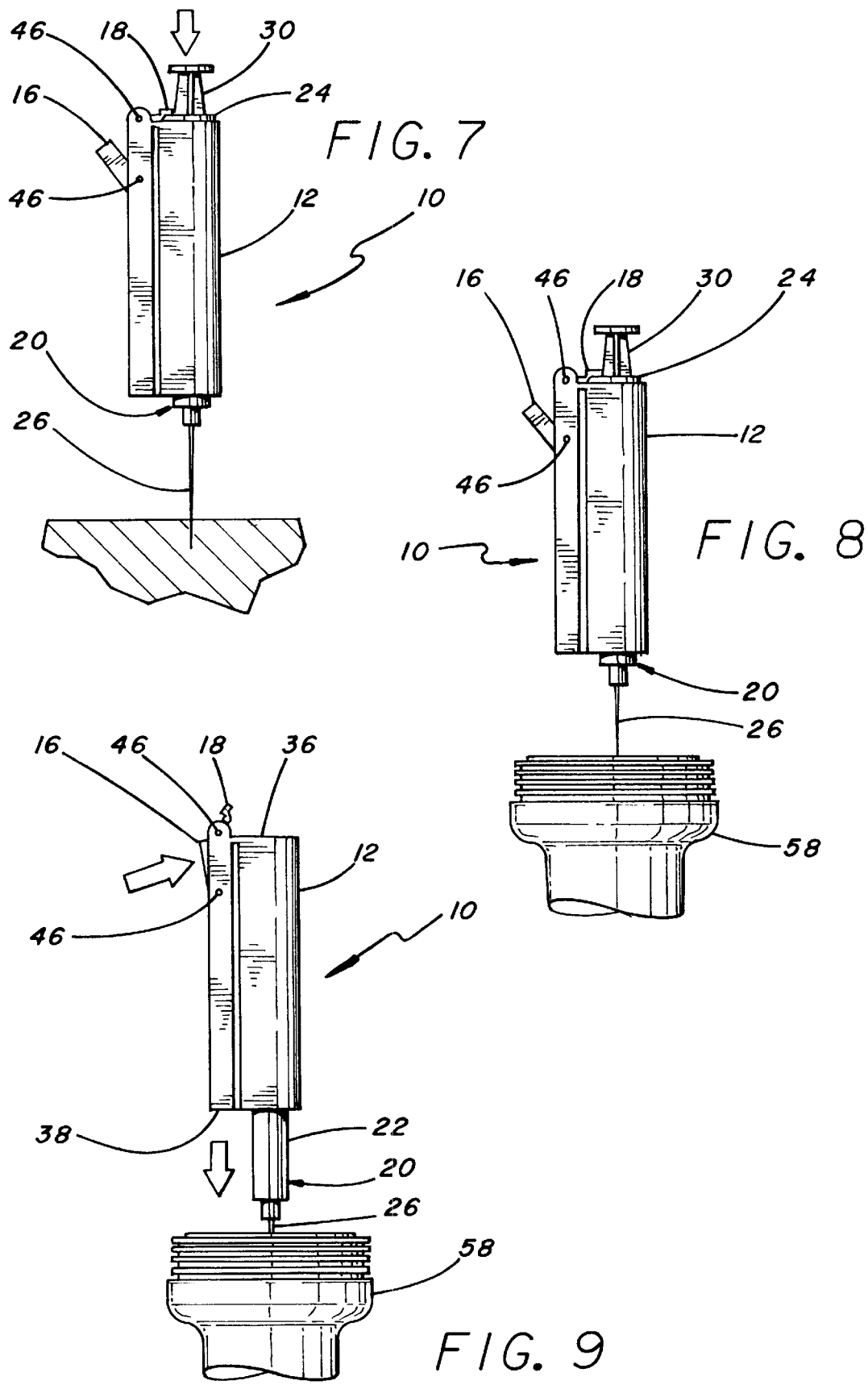

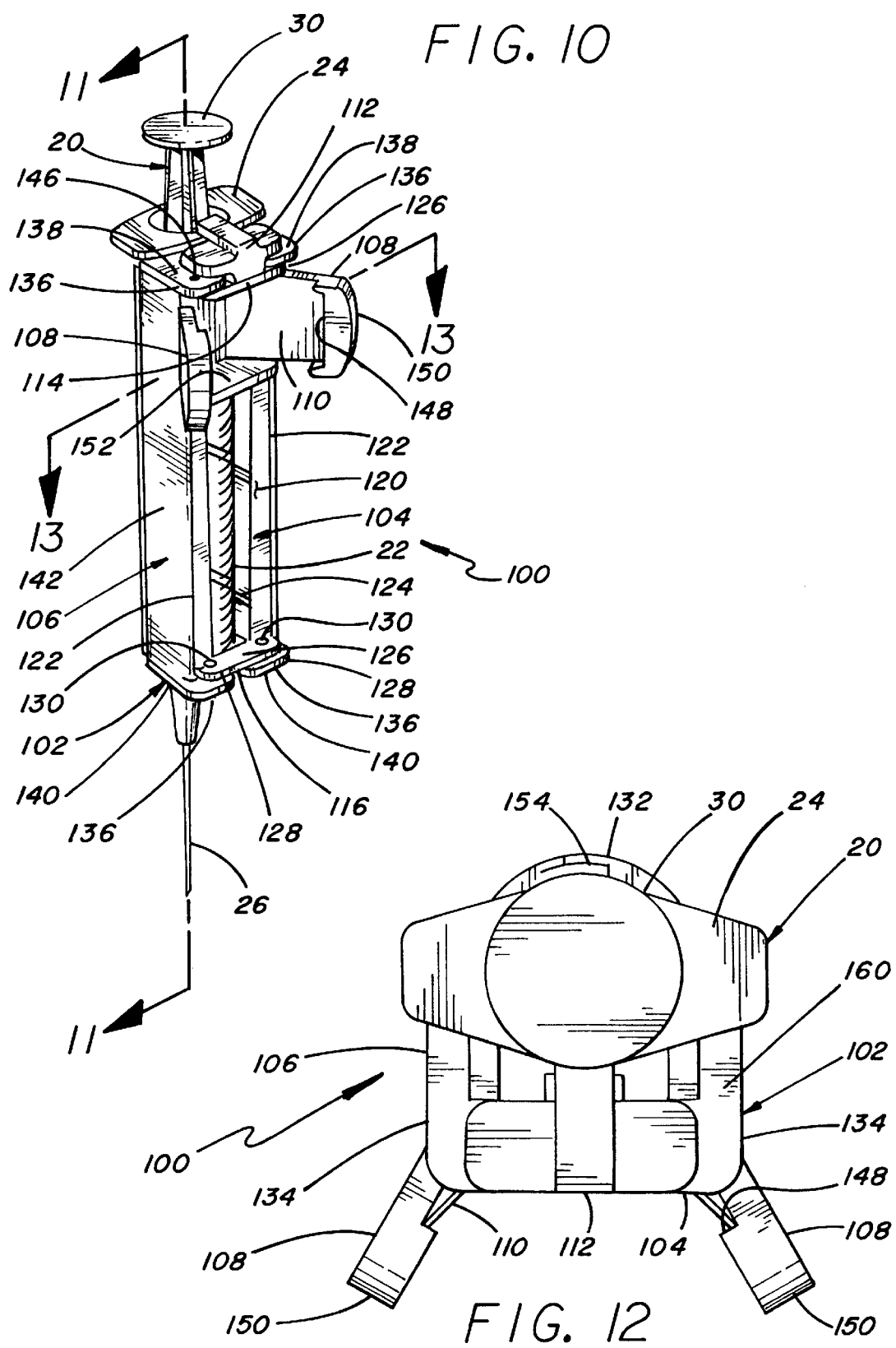

6,162,198

INJECTION SHIELD AND METHOD FOR DISCHARGING A SYRINGE CONTAINING RADIOACTIVE MATERIAL

This application is based upon and claims priority from provisional patent application Ser. No. 60/019,569, filed Jun. 11, 1996.

BACKGROUND OF THE INVENTION

The present invention generally relates to shielded containers for the handling of radioactive materials and, more particularly, to a radiation-resistant, or radiation-dense, shield allowing the improved handling and discharge of a syringe containing a radioactive material.

In the nuclear medical industry, radioactive drugs are used for various applications, including internal imaging of various physiological functions for diagnostic and therapeutic purposes. Over the years, the medical industry has developed many different radioactive drugs that are designed to facilitate imaging and treatment of physiological functions.

Generally, radioactive drugs are in a liquid form that is suitable for injection into a patient. Because of the radioactive characteristics of these drugs, they must be handled according to regulations promulgated by various departments of the United States government, including the Department of Transportation (DOT), the Nuclear Regulatory Commission (NRC), and the Occupational Health and Safety Administration (OSHA). Accordingly, hospitals that administer radioactive drugs to patients must invest in the equipment and the training necessary to meet the requirements of such regulations.

Typically, a patient requires only a small dose of a specific radioactive drug. Therefore, depending on the number of patients, it is generally not economical for one hospital to maintain the staff and equipment to produce the radioactive drugs required by its patients. Furthermore, the radioactive agents in the drugs have various half lives and thus lose their effectiveness to varying degrees as they age. Thus, if a hospital does not have the required demand, some of its inventory of radioactive agents may decay and become unusable. To avoid the expense of such in-house production of radioactive drugs, many health care providers now purchase each prescribed dose of a radioactive drug from an outside radiopharmacy.

The radiopharmacies which deliver radioactive drugs to hospitals utilize the principles of mass production to reduce their per-unit costs. The radiopharmacies receive prescription orders and deliver the corresponding radioactive drugs to nearby hospitals. The radiopharmacies fill each prescription by packaging each dose of radioactive drug in a syringe intended for a specific patient. The syringes containing the radioactive drugs must be carefully handled and delivered inside containers offering some degree of radiation shielding.

One type of delivery container currently used for the delivery of syringes containing radioactive drugs is known as a radiopharmaceutical pig. One type of radiopharmaceutical pig has an interior chamber lined with a radiation-shielding material, typically elemental lead, to safely enclose one syringe. This radiopharmaceutical pig is described in U.S. Pat. No. 5,519,931, issued to Syncor International Corporation and incorporated herein by reference.

Once the radiopharmaceutical pig containing the filled syringe arrives at the hospital, the syringe is removed for use. Because the syringe is radioactive, it is placed into a radiation-resistant shield to protect hospital workers from radiation exposure while they manipulate the syringe to inject the contents of the syringe into the patient. After the dose is injected into the patient, the syringe is referred to as "spent" although it generally contains a small amount of residual radioactive drug. In addition to the radioactive contamination, the hypodermic needle of the spent syringe is biologically contaminated from contact with the patient. If the radiopharmacy offers disposal services, the spent syringe may be placed back into the radiopharmaceutical pig for a return trip to the radiopharmacy.

One conventional syringe injection shield has a hollow cylindrical body with an upper opening for accepting the syringe and a lower opening through which the needle of the syringe projects when the syringe is inserted inside the shield. The shield is made of radiation resistant metal, such as tungsten, and also includes a lead glass window so that a hospital worker can view the amount of the drug within the syringe. A spring-biased lever is mounted in a slot in the side of the body. The lever extends inside the body to frictionally engage the syringe.

The body of the shield has a length commensurate with the length of the body of the syringe to allow the hypodermic needle and the plunger of the syringe to project from each end of the shield. Because the shield must allow the health care worker to position and discharge the syringe, the shield cannot interfere with the insertion of the needle into the patient and the downward movement of the plunger to inject the radioactive drug into the patient. As is commonly known, the upper portion of a syringe body has a base with flanges projecting radially outwardly therefrom. Because the flanged base of the syringe is somewhat larger than the upper opening of the shield, the syringe will not slip out of the shield as downward force is applied to the syringe's plunger. Because of the expense of radiation-resistant syringe shields, hospitals typically sterilize them for reuse.

The aforementioned syringe shield is generally effective. However, one drawback associated with this injection shield design is that with each use it is exposed to the biologically contaminated needle of the syringe and thus must undergo expensive advanced sterilization procedures before it can be reused. In particular, after the syringe is discharged, the syringe is removed from the shield and placed back in the radiopharmaceutical pig for disposal. Because the flanged base of the syringe is larger than the upper opening of the shield, the syringe can only be removed by withdrawing it in an upward direction, thereby causing the contaminated needle to pass back through the inside the shield as the syringe and shield are separated. Therefore, as the spent syringe is removed from the shield, the contaminated needle can touch the inside surface of the shield. Accordingly, expensive advanced sterilization procedures must be employed upon the shield before it can be reused. Such a process is expensive and, therefore, undesirable.

Accordingly, there exists a need for an injection shield and method for discharging a syringe containing radioactive material that avoids the need for the aforementioned expensive sterilization procedures. The present invention satisfies this need and provides further related advantages.

SUMMARY OF THE INVENTION

Briefly, and in general terms, the present invention resides in an injection shield and method for discharging a syringe containing radioactive material that avoids the need for expensive sterilization procedures. The invention allows a health care worker to safely inject the contents of the syringe into a patient by inserting the syringe into a predetermined position within the radiation-dense injection shield. Once inserted, the syringe is secured within the shield so that the plunger of the syringe projects from one end of the shield in a predetermined direction. The shield and syringe are then moved to another position and the contents of the syringe are injected while the syringe is within the shield. The spent syringe can then be released from the shield in a direction away from the direction in which the plunger of the syringe projects, thereby avoiding contamination of the shield from contact with the needle. Significantly, the shield can be reused without expensive sterilization procedures.

More specifically, and by way of example only, the injection shield is used in conjunction with a syringe containing radioactive material. In one embodiment, the syringe has a tubular body with a needle mounted upon an opening in one end of its body and a plunger mounted in an opening in the other end of its body. The shield has a wall portion with a radiation-dense window mounted therein. A radiation-dense jaw is pivotally mounted to the wall portion of the shield to move between an open position and a closed position. In the closed position, the jaw cooperates with the wall portion to circumferentially enclose the radioactive material within the body of the syringe and the plunger of the syringe projects from the shield in a predetermined direction. In the open position, the jaw is separated from the wall portion of the shield a distance sufficient to allow the syringe to move away from the shield in a direction away from the direction in which the syringe plunger is oriented when the jaw is in the closed position.

In another aspect of the invention, an injection shield is provided that includes a wall portion having opposing side edges and radiation-dense window mounted therebetween. The shield also has two radiation-dense jaws that each have a far side edge and a near side edge. The far side edge of each jaw is located away from the wall portion and each jaw is pivotally mounted to the wall portion to locate the near side edge of the jaw adjacent to an associated side edge of the wall portion. The jaws are pivotally mounted on the wall portion for movement between an open position and a closed position.

In the closed position, the free side edges of the jaws abut each other and cooperate with the wall portion to circumferentially enclose the radioactive material within the body of the syringe. In this closed position, the plunger of the syringe projects from the shield in a predetermined direction. In the open position, the free side edges of the jaws separate from each other a predetermined distance to allow the syringe to move from the shield in a direction away from the direction in which the plunger of the syringe projects in the closed position, thereby avoiding contamination of the shield from contact with the needle In a more detailed aspect of the invention, the free edges of the jaws define cooperating notches to allow the jaws to overlap in the closed position. In another such detailed aspect, the shield also includes a stop mounted on the wall portion. The stop has an arm projecting toward the free edges of the jaws and is sized to extend above the flanged base of the syringe. In yet another detailed aspect, the shield has opposing finger tabs. One finger tab is mounted upon each jaw for operation of the jaws. A spring can be located between the jaws or between the finger tabs to bias the jaws toward the closed position.

In another embodiment of the invention, an injection shield is provided for a syringe containing a radioactive material. The syringe having a body, a needle and a plunger. The shield comprises a shield body and a release mechanism. The shield body has a radiation-dense wall defining a holder having opposing ends. Each end of the holder has an opening formed therein and a passage therebetween sized to accept the body of the syringe. The release mechanism is carried by the body and the release mechanism selectively retains the syringe body in the passage of the holder with the syringe plunger projecting from one end of the holder and the syringe needle projecting from the other end of the holder for administration of the radioactive material to a patient. The release mechanism is selectively operable to release the spent syringe from the shield in a direction other than the direction of the syringe plunger, thereby avoiding contamination of the shield from contact with the syringe needle.

Because the invention allows a spent syringe to fall away from the shield in a direction away from that of the syringe plunger, there is no danger that the needle will contact the shield and contaminate it. Accordingly, expensive sterilization procedures are not required before the reuse of the injection shield.

Other features and advantages of the present invention will become apparent from the following description of the preferred embodiment, taken in conjunction with the accompanying drawings, which illustrate, by way of example, the principles of the invention.

BRIEF DESCRIPTION OF THE DRAWINGS

The following drawings illustrate a presently preferred embodiment of the invention, in which:

FIG. 3 is a top view showing the injection shield and syringe of FIG. 1;

FIG. 4 is partial cross sectional view of a radiopharmaceutical pig and syringe containing radioactive material;

FIG. 5 is an elevational view of the insertion of the syringe of FIG. 4 into the injection shield of FIG. 1;

FIG. 6 is an elevational view of the syringe of FIG. 4 after its insertion into the injection shield of FIG. 1;

FIG. 7 is an elevational view of the discharge of the syringe of FIG. 4 after its insertion into the injection shield of FIG. 1;

FIG. 8 is an elevational view of the syringe of FIG. 4 and the injection shield of FIG. 1 positioned above a portion of the radiopharmaceutical pig of FIG. 8;

FIG. 9 is an elevational view of the release of the syringe of FIG. 4 from the injection shield of FIG. 1;

FIG. 10 is a perspective view of a second embodiment of an injection shield and syringe;

FIG. 12 is a top view showing the injection shield and syringe of FIG. 10;

DESCRIPTION OF THE PREFERRED EMBODIMENT

Figure 1:
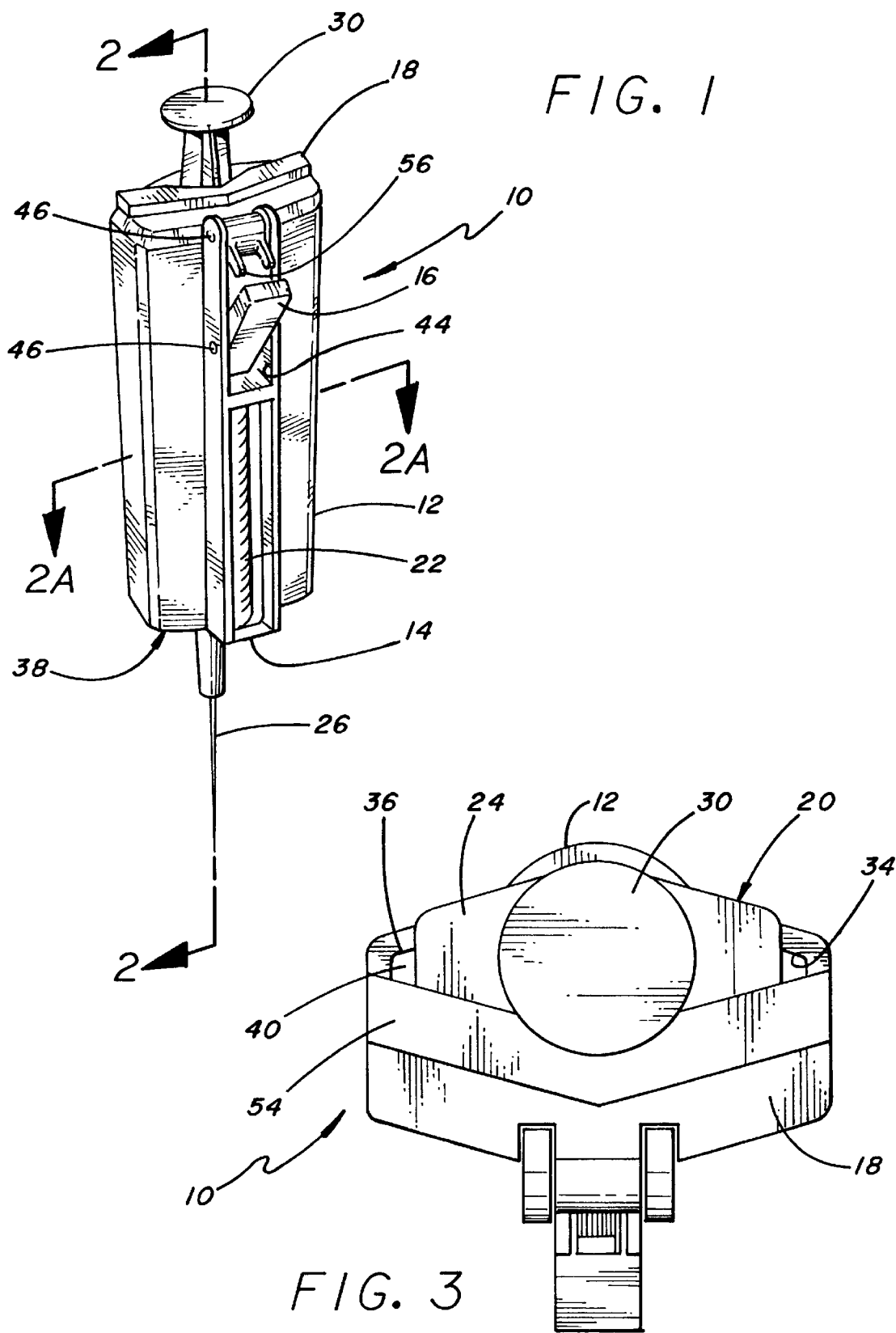
FIG. 1 is a perspective view of a first embodiment of an injection shield and syringe.
Figures 2, 2A:
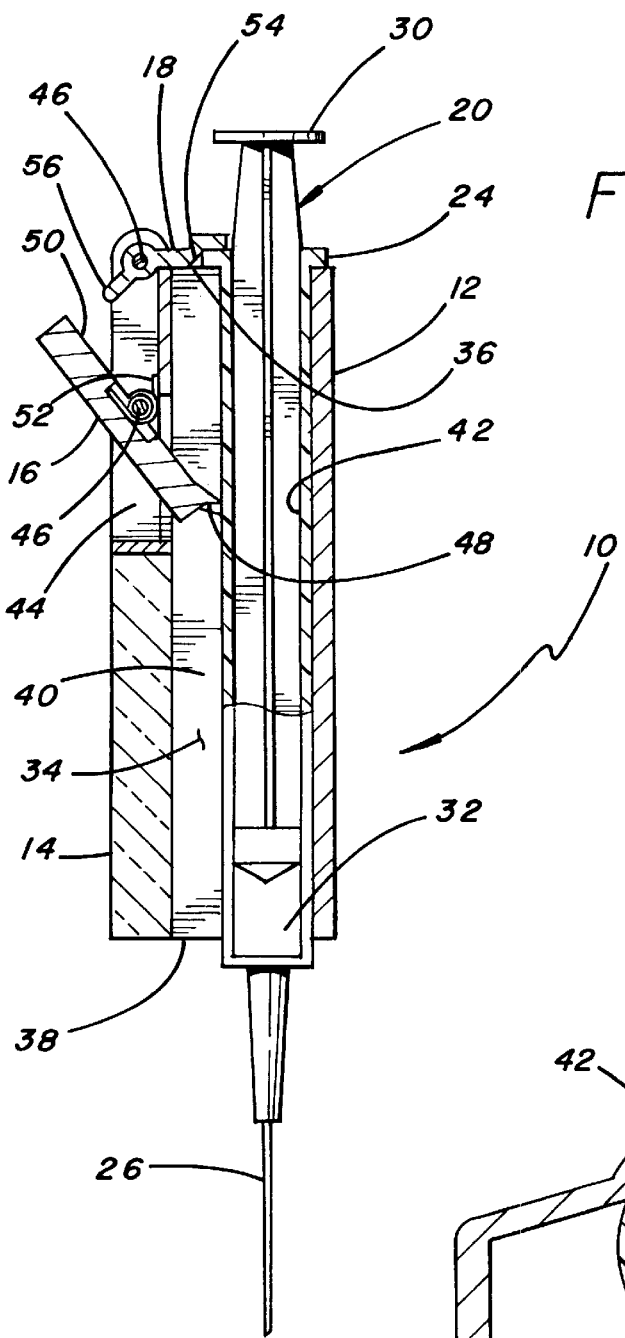
FIG. 2 is a cross sectional view showing the injection shield and syringe along line 2—2 of FIG. 1.
FIG. 2A is a cross sectional view showing the injection shield and syringe along line 2A—2A of FIG. 1.
Figures 11, 13:
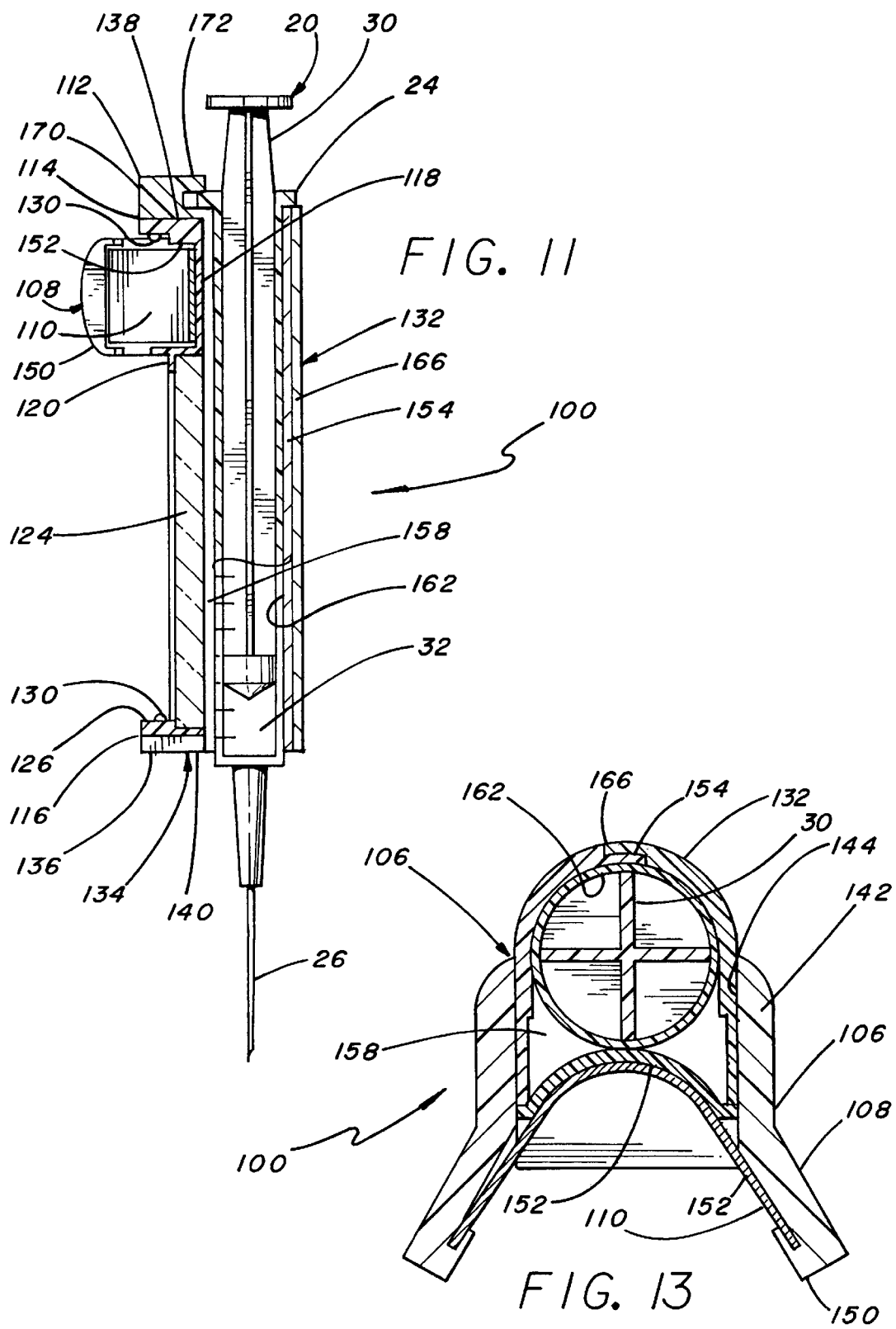
FIG. 11 is a cross sectional view showing the injection shield and syringe along line 11—11 of FIG. 10.
FIG. 13 is a cross sectional view showing the injection shield and syringe along line 13—13 of FIG. 10.
Figure 14:
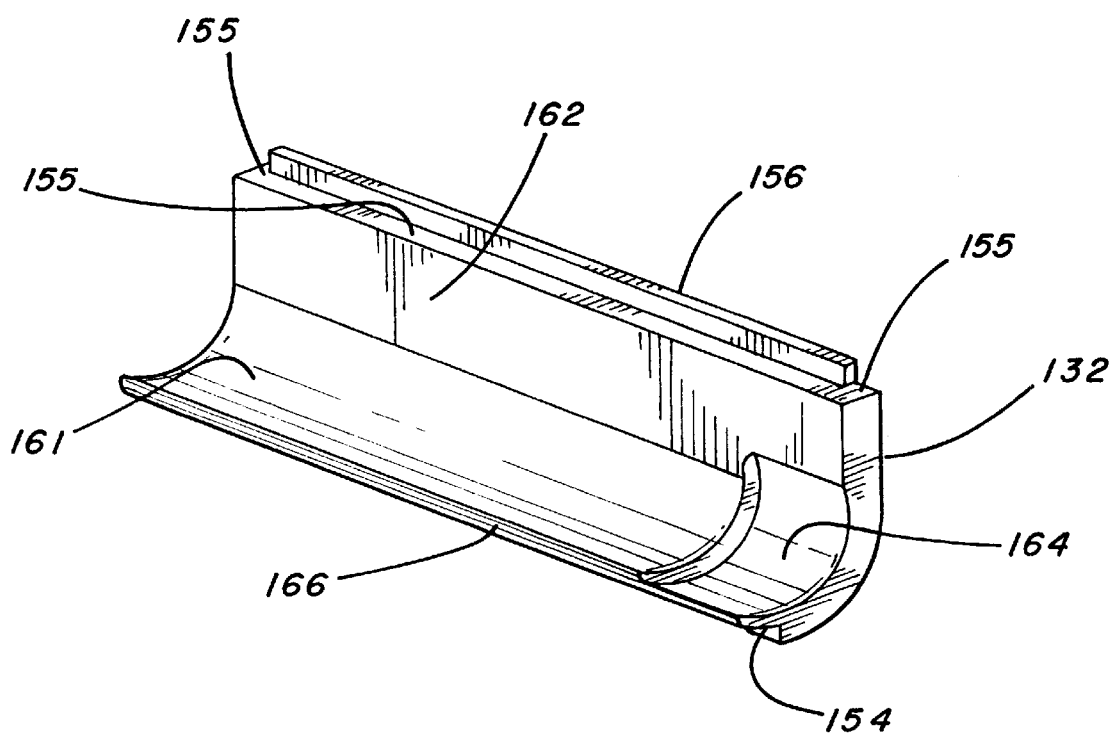
FIG. 14 is a perspective view of a flap from the injection shield of FIG. 10.
Figures 15, 16, 17:
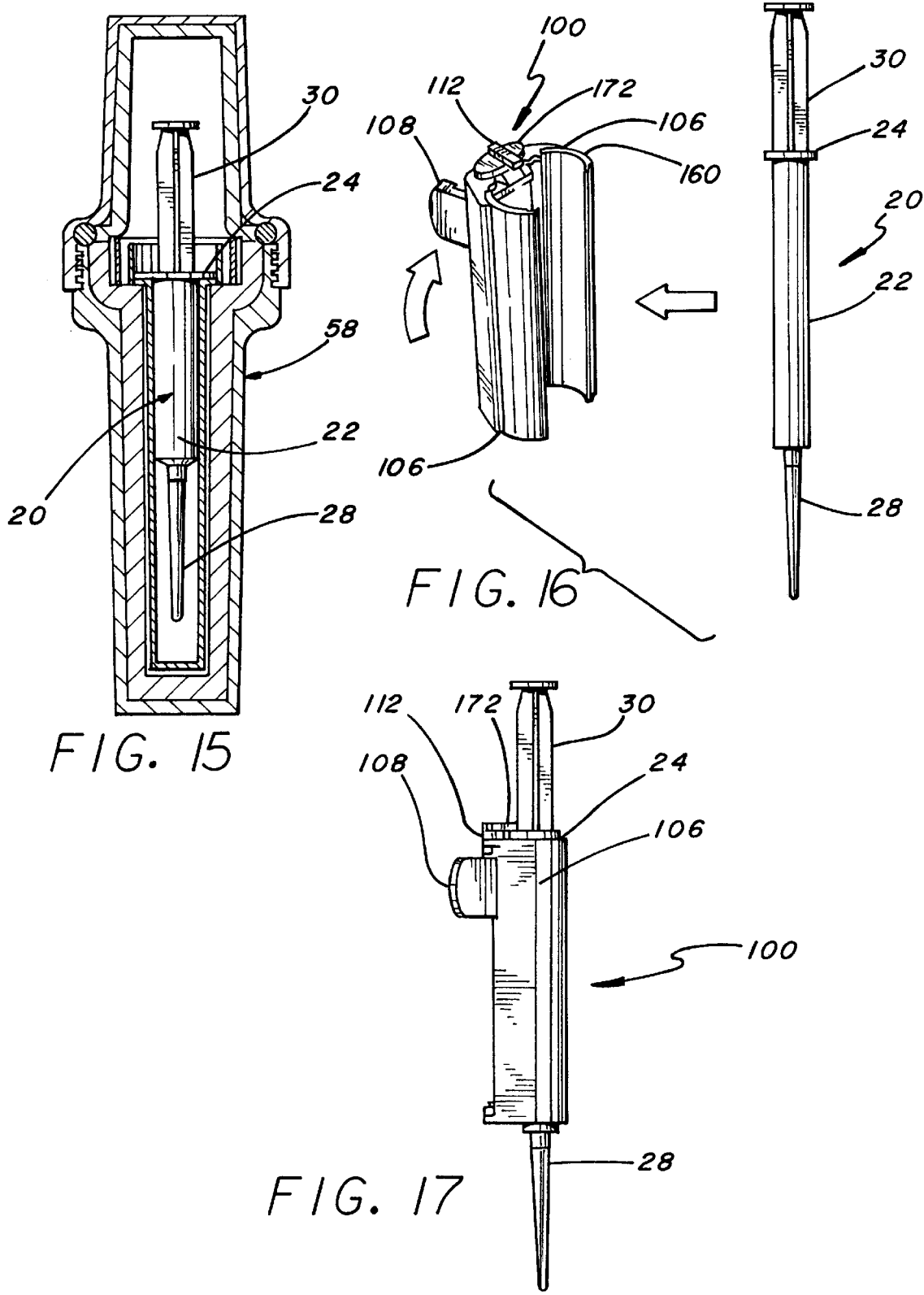
FIG. 15 is partial cross sectional view of a radiopharmaceutical pig and syringe containing radioactive material.
FIG. 16 is an elevational view of the insertion of the syringe of FIG. 15 into the injection shield of FIG. 10.
FIG. 17 is an elevational view of the syringe of FIG. 15 after its insertion into the injection shield of FIG. 10.
Figure 18:
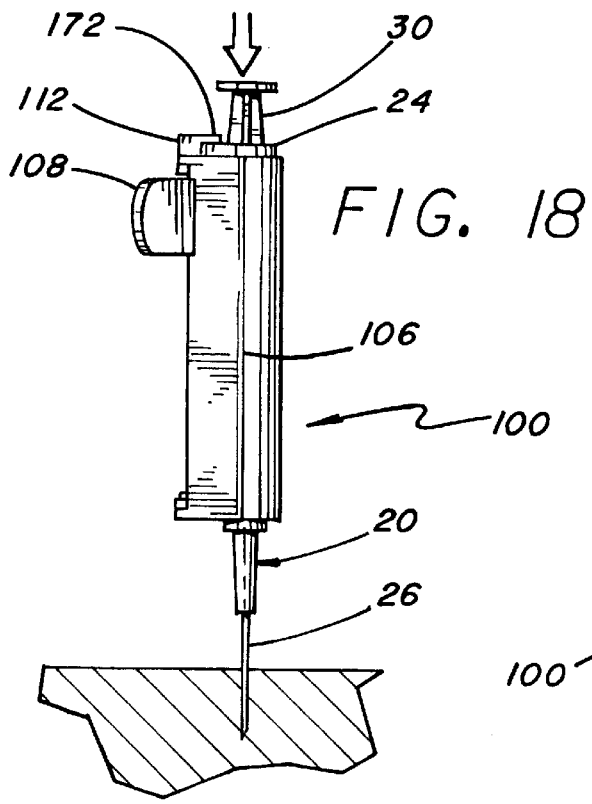
FIG. 18 is an elevational view of the discharge of the syringe of FIG. 15 after its insertion into the injection shield of FIG. 10.
Figure 19:
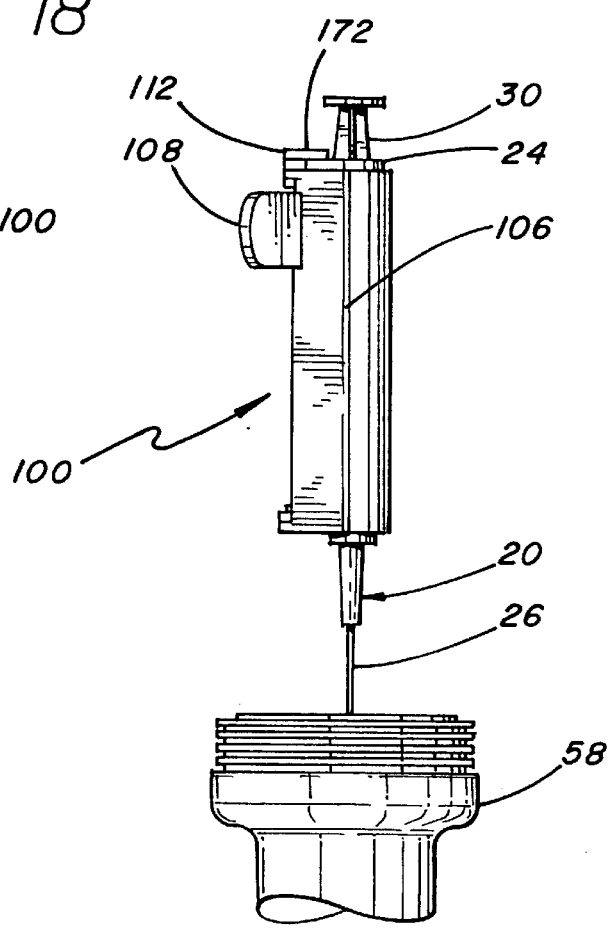
FIG. 19 is an elevational view of the syringe of FIG. 15 and the injection shield of FIG. 10 positioned above a portion of the radiopharmaceutical pig of FIG. 15.
Figure 20:
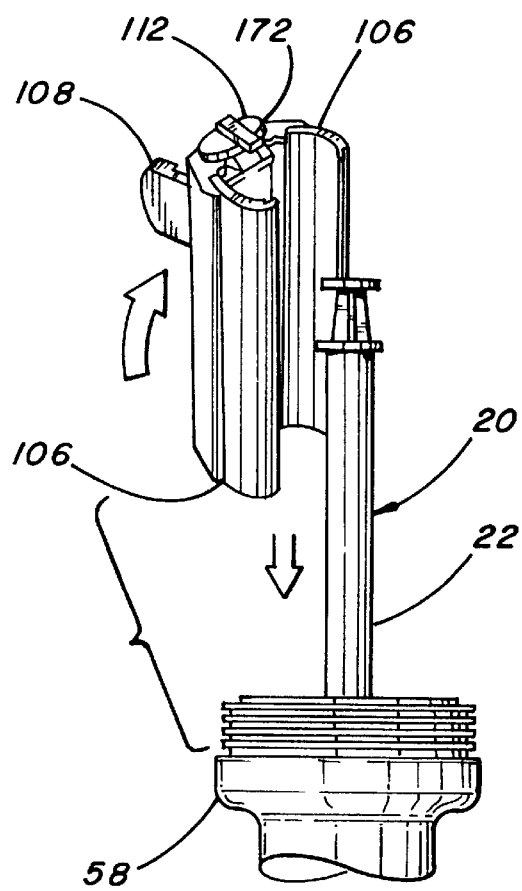
FIG. 20 is an elevational view of the release of the syringe of FIG. 15 from the injection shield of FIG. 10.

Referring now to the drawings, and particularly to FIGS. 1–3 thereof, there is shown one embodiment of a hollow injection shield, generally referred to by the reference numeral 10, in accordance with the present invention. The injection shield 10 has a tubular body 12 with a rectangular lead-glass window 14, a rectangular pivoting release tab 16 and a pivoting top 18. The shield 10 holds a syringe 20 in a manner that allows for discharge of the syringe without its removal from the shield. After discharge, the spent syringe can advantageously be removed from the shield without risking contamination of the shield, as described below.

As shown in FIG. 2, the syringe 20 is a commonly available disposable medical type of a 3 cubic centimeter size. The syringe also can be of other sizes, as required by particular applications. The syringe has a generally tubular body 22 with a flanged base 24, a hypodermic needle 26, a cap 28, and a plunger 30. The syringe contains a radioactive material 32 for injection into a patient.

The tubular body 12 of the shield 10 has an interior surface 34 defining an upper opening 36, a lower opening 38, and an internal passage 40 therebetween. The interior surface of the shield body 12 also defines a groove 42 between the upper and lower openings. The groove is sized to cradle the body 22 of the syringe 20 to hold the syringe in the shield. The diameter of the groove is slightly smaller than the flanged base 24 of the syringe so that the syringe will not move during the discharge process (i.e., when downward force is applied to the plunger 30). However, the remainder of the passage 40 through the body 12 is sized not to obstruct the flanged base 24 of the syringe, thereby allowing the syringe to freely pass through the entire shield 10 once the syringe is moved laterally out of the groove 42. The length of the passage 40 generally is the same as the length of the syringe body 22. The interior surface 34 of the shield is painted white to provide a neutral background that facilitates the viewing of the syringe through the lead glass window 14. Other than the lead-glass window, the components of the shield can be made from tungsten or other suitable radiation-dense material.

The lead-glass window 14 is mounted in the body 12 of the shield 10 adjacent to the lower opening 38 to allow the user to view the amount of drug within the body 22 of the syringe 20. The lead-glass window is approximately 0.25 inch thick and can be made of lead glass having a lead density of approximately 5.2 grams per cubic centimeter.

The body 12 of the shield 10 also has a slot 44 adjacent to the upper opening 36 and above the lead-glass window 14. The slot is sized to accept the release tab 16 and the pivoting top 18 of the shield. Pivot pins 46 enable the tab and the top to rotate. The release tab is generally rectangular and has lower edge 48 to frictionally engage the syringe body 22 and an upper striking surface 50 to engage the pivoting top, as described below. A coil spring 52 is mounted between the release tab and the body of the shield to bias the lower edge 48 of the tab toward the syringe.

The pivoting top 18 of the shield 10 has a raised lip 54 located adjacent to the syringe base 24 and two legs 56 located adjacent to the release tab 16. The legs are sized to engage the release tab when the release tab is depressed, thereby causing the top to pivot upwardly away from the upper opening 36 of the shield body 12. The raised lip of the top is sized to engage the flanged base 24 of the syringe 20 to hold the syringe in the groove 42 of the shield body.

In operation, the injection shield 10 offers a level of radiation protection to health care workers while the radioactive drug is administered to the patient. As shown in FIGS. 4–9, the syringe 20 containing the radioactive drug 32 can arrive at the hospital in a radiopharmaceutical pig 58. After the syringe is removed from the pig, the administering health care worker depresses the release tab 16 and places the syringe into the shield so that the flanged base 24 of the syringe abuts the upper opening 36 of the shield body 12 and rests in the groove 42. When the release tab is depressed, its striking surface 50 engages the legs 56 of the top 18, thereby causing the top to pivot upwardly to provide clearance for the syringe as it moves into the shield.

Thereafter, the health care worker releases the release tab 16 and the force of the spring 52 pivots the tab into is resting position whereby the lower edge 48 of the tab engages the syringe 20. The release of the tab also frees the legs 56 of the top 18 to allow the top to pivot downward until it rests on top of the flanged base 24 of the syringe. The cap 28 of the syringe is then removed and, while the health care worker holds the top 18 of the shield against the flanged syringe base, the syringe can be positioned for injection of the drug into the patient. To inject the drug, the health care worker holds the shield so that he or she can view the contents of the syringe through the lead-glass window 14 and simultaneously depress the plunger 30 of the syringe.

After the contents of the syringe 20 have been injected into the patient, the shield 10 is positioned above the open radiopharmaceutical pig 58 containing a SECURE brand safety insert so that the contaminated needle 26 of the syringe points into the pig. Recapping of the syringe is not recommended because of the risk that the health care worker might mishandle the cap 28 and instead suffer a needle stick from the contaminated needle of the syringe. The release tab 16 is then depressed, causing the top 18 of the shield to pivot upward and release the syringe 20, which falls through the passage 40 of the shield and into the pig. The pig is then assembled and sent away for disposal of the syringe.

Because the design of the shield 10 allows the spent syringe 20 to fall away from the shield in the direction of the needle 26, the risk that the hypodermic needle will contaminate the shield by contact is minimized. Accordingly, expensive advanced sterilization procedures are not needed before the injection shield 10 can be reused.

A second embodiment of the present invention is shown in FIGS. 10–14 as a clam-shell injection shield 100. This injection shield is intended to shield the syringe 20 already described above. The clam-shell injection shield 100 has a body 102 with a back wall 104 pivotally mounted to two curved jaws 106. Each jaw has a finger tab 108 for opening and closing the jaw. A leaf spring 110 between the finger tabs biases the jaws toward a closed position. A stop 112 is mounted on top of the back wall to restrain any upward movement of the syringe while its needle 26 is inserted into the patient. The shield holds the syringe in a manner that allows for discharge of the syringe without its removal from the shield. After discharge, the spent syringe can advantageously be removed from the shield without risking contamination of the shield, as described below.

The back wall 104 of the shield 100 has an upper end 114, a lower end 116, an inside surface 118, an outside surface 120, and two side edges 122. A rectangular lead-glass window 124 is mounted adjacent to the lower end of the back wall for viewing the contents of the syringe 20. At each end of the back wall, L-shaped projections 126 extend from the outside surface of the wall to define opposing holes 128 to receive pivot pins 130. The back wall can be made of ABS plastic by an injection molding process or can be made of tungsten by a sintered powder metallurgy process, depending on the level of shielding required for a specific application. The back wall can be made by other well known manufacturing processes from other materials having radiation dense properties suitable for a particular application. The lead-glass window can be made of 0.250 inch lead glass having a density of 5.2 grams of lead per cubic centimeter. The window can be made to other thicknesses and densities as required by particular applications.

Each jaw 106 has a curved tungsten flap 132 mounted to an associated hinge piece 134. The hinge piece has hinge projections 136 at its upper and lower ends 138 and 140 and a wall 142 extending therebetween along the length of the hinge piece. The wall of each hinge piece has an inside surface 144 located in opposed alignment with the inside surface of the other hinge piece. The curved flaps 132 are mounted to the inside surfaces of the hinge pieces, as described in more detail below. Each hinge projection 136 has a pivot pin hole 146 located to align with an associated one of the pivot pin holes 128 in the L-shaped projections 126 of the back wall 104. The hinge projections of each hinge piece are spaced apart a distance sufficient to fit around the upper and lower ends 114 and 116 of the back wall. The hinge piece 134 is made from injection molded ABS plastic or other suitable material. It should be noted that the components of the shield 100 can be made of other radiation dense materials well known in the art.

Each finger tab 108 projects from its associated hinge piece 134 in a direction outward from the outside surface 120 of the back wall 104 of the shield 100. The finger tabs enable the user to open and close the flaps 132 to operate the shield. The finger tabs are located in opposed alignment above the lead-glass window 124. The tabs have cooperating notches 148 on their outer ends 150 to hold the metal leaf spring 110 therebetween to bias the jaws 106 against each other. The back wall of the shield defines a depression 152 located between the finger tabs to accommodate the center portion of the curved leaf spring 110.

Each curved flap 132 is mounted along the inside surface 118 of the wall 142 of an associated hinge piece 134. A notch 154 is formed in the near edge 155 of the flap adjacent to the back wall 104 to provide a mating tab 156 that fits between the hinge projections 136 on the associated hinge piece 134. The curved flaps are approximately 0.130 inch thick and have a diameter sized provide an interior space 158 between the flaps and the back wall 104 to enclose or, alternatively, frictionally engage, the cylindrical body 22 of the syringe 20 therein under the force provided by the leaf spring 110. Alternatively, if less shielding is required for a particular application, the flaps can be approximately 2.2 millimeters thick. The flaps are made of tungsten and can be formed by using a sintered powder metallurgy manufacturing process. Because the flanged base 24 of the syringe is held between the upper end 160 of the body 102 and the stop 112, frictional engagement between the flaps and the syringe is optional. A layer of white plumber's tape 161 is located on the inside surface 162 of each flap to provide a neutral background that facilitates the viewing of the syringe 20 through the lead glass window 124. The upper portion of the inside surface of each flap has an area of slightly greater diameter 164 to accommodate a section of increased diameter in the upper portion of the syringe body 22.

The outer or free edges 166 of the flaps 132 are notched 168 so that the flaps can overlap each other when the free edges of the flaps abut in the closed position. The flaps overlap in this manner to shield the radiation emitted by the radioactive drug in the body 12 of the syringe 20. The flaps are fastened to the hinge pieces 134 by adhesive. However, other bonding processes or mechanical fasteners well known in the art can be used to fasten each hinge piece to its associated flap. Further, the hinge piece and the flap could be of a one piece construction.

The stop 112 has a base 170 and an upper arm 172 sized to project over the flanged base 24 of the syringe 20. The base of the stop is sized to fit between the hinge projections 136 abutting the upper end 114 of the back wall 104. The stop is preferably made of injection molded ABS plastic and is fastened to the upper end of the back wall by adhesive, although other suitable materials and fasteners can be used according to the requirements of a particular application.

In operation, the injection shield 100 offers a level of radiation protection to health care workers while the radioactive drug is administered to the patient. As shown in FIGS. 15–20, the syringe 20 containing the radioactive drug can arrive at the hospital in a radiopharmaceutical pig 58. After the syringe is removed from the pig, the administering health care worker compresses the finger tabs 108 toward each other to cause the jaws 106 of the shield 100 to open. The worker then aligns the syringe with the body 102 of the shield and inserts the syringe into a position between the jaws so that the flanged base 24 of the syringe is located between the arm 172 of the stop and the upper ends of the jaws 106.

Thereafter, the health care worker releases the finger tabs 108 and the force of the leaf spring 110 pivots the jaws 106 into the closed position, where the free ends 166 of the flaps 132 engage each other to enclose the circumference of the syringe body 22 within the space between the inside surface 118 of the back wall 104 and the flaps. The cap 28 of the syringe is then removed and the syringe and shield are positioned for injection of the drug into the patient. While the needle 26 is inserted, the arm 172 of the stop 112 prevents the insertion force from pushing the syringe 20 out of the shield 100. To inject the drug, the health care worker holds the shield so that he or she can view the contents of the syringe through the lead-glass window 124 and simultaneously depresses the plunger 30 of the syringe.

After the contents of the syringe 20 have been injected into the patient, the shield 100 is positioned above the open radiopharmaceutical pig 58 so that the contaminated needle 26 of the syringe points into the pig. The finger tabs 108 are then depressed, causing the jaws 106 of the shield to pivot open and release the syringe, which falls from the shield into the pig. The pig is then assembled and sent away for disposal of the syringe. Recapping of the syringe is not recommended because of the risk that the health care worker may mishandle the cap and suffer a needle stick from the contaminated needle of the syringe.

Like the first embodiment, because the design of the shield 100 allows the spent syringe 20 to fall away from the shield in the direction of the needle 26, the risk that the needle will contaminate the shield 100 by contact is minimized. Accordingly, expensive advanced sterilization procedures are not needed before the injection shield 100 can be reused. The design of the shield 100 also is more compact compared to the first embodiment 10 and thus is more easily manipulated when the health care worker is trying to insert the needle of the shielded syringe into the patient. The pivoting jaws of the shield 100 also allow the syringe to be more easily removed from the shield 100.

While particular forms of the invention have been illustrated and described, it will be apparent that various modifications can be made without departing from the spirit and scope of the invention. Accordingly, it is not intended that the invention be limited, except as by the claims to be filed in this matter.

We claim:

1. An injection shield for a syringe containing radioactive material, the syringe having a tubular body with a needle mounted upon an opening in one end of the body and a plunger mounted in an opening in the other end of the body, the injection shield comprising:

a radiation-dense body having at least one radiation-dense jaw extending substantially the length of the tubular body of the syringe, the jaw mounted to move between an open position and a closed position, wherein in the closed position, the jaw abuts the body to shield at least a portion of the radioactive material within the body of the syringe and the plunger of the syringe projects from the shield in a predetermined direction, and wherein in the open position, the jaw moves to a predetermined position to allow the syringe to move in a direction away from the direction in which the syringe plunger is oriented when the jaw is in the closed position.

2. The injection shield as defined in claim 1, further comprising a second jaw mounted to move between an open position and a closed position, wherein in the closed position, the second jaw cooperates with the first jaw to shield at least a portion of the radioactive material within the body of the syringe, and in the open position, the second jaw allows the syringe to move in a direction away from the direction in which the syringe plunger is oriented when the first jaw is in the closed position.

3. The injection shield as defined in claim 2, wherein each jaw includes a free side edge having a projection, the edge of one jaw defining a notch sized to mate with the projection on the edge of the other jaw when the jaws are in the closed position.

4. The injection shield as defined in claim 2, further comprising opposing finger tabs mounted upon each jaw.

5. The injection shield as defined in claim 2, further comprising a spring biasing the jaws to the closed position.

6. The injection shield as defined in claim 1, wherein the body further comprises a radiation-dense wall portion having a radiation-dense window mounted therein, wherein the jaw is pivotally mounted to the wall portion so that, when in the closed position, the jaw and the wall portion cooperatively shield at least a portion of the radioactive material within the body of the syringe.

7. The injection shield as defined in claim 6, further comprising a second jaw mounted to the wall portion to move between an open position and a closed position, wherein in the closed position, the second jaw cooperates with the first jaw and the wall portion to shield at least a portion of the radioactive material within the body of the syringe, and in the open position, the second jaw allows the syringe to move in a direction away from the direction in which the syringe plunger is oriented when the first jaw is in the closed position.

8. The injection shield as defined in claim 6, wherein the body further comprises a stop having an arm projecting inwardly and sized to extend above the end of the syringe body from which the plunger projects.

9. The injection shield as defined in claim 3, further comprising a finger tab located upon the jaw.

10. An injection shield for a syringe containing radioactive material, the syringe having a tubular body with a needle mounted on an opening in a first end of the body and a plunger mounted in an opening in a second end of the body, the second end of the body having a flange thereon, the injection shield comprising:

a radiation-dense body having at least one radiation-dense jaw, the jaw having an upper edge and mounted to move between an open position and a closed position;

wherein, in the closed position, at least a portion of the upper edge of the jaw is disposed beneath the flange of the syringe, with the flange abutting the upper edge of the jaw, and the plunger of the syringe projects from the shield in a predetermined direction; and wherein in the open position, the jaw moves to a predetermined position such that the upper edge of the jaw is not disposed beneath the flange of the syringe to allow the syringe to move in a direction away from the direction in which the syringe plunger is oriented when the jaw is in the closed position.

11. The injection shield as defined in claim 10, further comprising a second jaw mounted to move between an open position and a closed position, wherein in the closed position, the second jaw cooperates with the first jaw to shield at least a portion of the radioactive material within the body of the syringe, and in the open position, the second jaw allows the syringe to move in a direction away from the direction in which the syringe plunger is oriented when the first jaw is in the closed position.

12. The injection shield as defined in claim 11, wherein each jaw includes a side edge having a projection, the side edge f one jaw defining a notch sized to mate with the projection on the side edge of the other jaw when the jaws are in the closed position.

13. The injection shield as defined in claim 11, further comprising opposing finger tabs mounted on each jaw.

14. The injection shield as defined in claim 11, further comprising a spring biasing the jaws to the closed position.

15. The injection shield as defined in claim 10, wherein the body further comprises a radiation-dense wall portion having a radiation-dense window mounted therein, wherein the jaw is pivotally mounted to the wall portion so that, when in the closed position, the jaw and the wall portion cooperatively shield at least a portion of the radioactive material within the body of the syringe.

16. The injection shield as defined in claim 15, further comprising second jaw mounted to the wall portion to move between an open position and a closed position, wherein in the closed position, the second jaw cooperates with the first jaw and the wall portion to shield at least a portion of the radioactive material within the body of the syringe, and in the open position, the second jaw allows the syringe to move in a direction away from the direction in which the syringe plunger is oriented when the first jaw is in the closed position.

17. The injection shield as defined in claim 15, further comprising a stop located on the shield body, the stop having an arm projecting inwardly and sized to extend above the flange on the syringe.

18. The injection shield as defined in claim 10, further comprising a finger tab located on the jaw.

19. An injection shield for a syringe containing radioactive material, the syringe having a tubular body with a needle mounted upon an opening in one end of the body and a plunger mounted in an opening in the other flanged end of the body, the injection shield comprising, a wall portion having opposing side edges; and two radiation-dense jaws, each jaw having a far side edge and a near side edge, the far side edge located away from the wall portion, each jaw pivotally mounted to the wall portion to locate the near side edge of the jaw adjacent to an associated side edge of the wall portion, the jaws pivotally mounted for movement between an open position and a closed position, wherein in the closed position, the far side edges of the jaws abut each other and cooperate with the wall portion to circumferentially enclose the radioactive material within the body of the syringe, the plunger of the syringe projecting from the shield in a predetermined direction, and in the open position, the far side edges of the jaws separate from each other a predetermined distance to allow the syringe to move away from the shield in a direction away from the direction in which the syringe plunger is oriented when the jaws are in the closed position.

20. The injection shield as defined in claim 19, wherein the far edges of the jaws define cooperating notches to allow the jaws to overlap in the closed position.

21. The injection shield as defined in claim 19, further comprising a stop mounted on the wall portion, the stop having an arm projecting toward the far edges of the jaws and sized to extend above the flanged end of the syringe body.

22. The injection shield as defined in claim 19, further comprising opposing finger tabs mounted upon each jaw.

23. The injection shield as defined in claim 19, further comprising a spring mounted adjacent to the jaws to bias the jaws to the closed position.

24. The injection shield as defined in claim 19, wherein the wall portion includes a window mounted therein.

25. An injection shield for a syringe containing radioactive material, the syringe having a tubular body with a needle mounted upon an opening in one end of the body and a plunger mounted in an opening in the other end of the body adjacent to a flange, the injection shield comprising:

a wall portion having opposing side edges and a radiation-dense window mounted therebetween;

a stop mounted on the wall portion, the stop having an arm extending above the flange of the syringe;

two radiation-dense jaws, each jaw having a far side edge and a near side edge and a finger tab, the far side edge located away from the wall portion, each jaw pivotally mounted to the wall portion to locate the near side edge of the jaw adjacent to the wall portion and to selectively move the jaw between an open position and a closed position, wherein in the closed position, the far side edges of the jaws abut each other in opposed alignment and cooperate with the wall portion to circumferentially enclose the radioactive material within the body of the syringe, the plunge of the syringe projecting from the shield in a predetermined direction, wherein the open position, the far side edges of the jaws separate from each other a predetermined distance to allow the syringe to move away from the shield in direction away from the direction in which the syringe plunger is oriented when the jaws are in the closed position;

a finger tab mounted to each jaw; and a spring located between the finger tabs to bias the jaws to the closed position.

26. The injection shield as defined in claim 25, wherein the far edges of the jaws define cooperating notches to allow the jaws to overlap in the closed position.

27. A method of injecting the contents of a syringe containing a radioactive material, the syringe having a needle and a plunger, the method comprising:

inserting the syringe into a predetermined position within a radiation-dense injection shield sized to allow the needle to project from the shield in one direction and the plunger of the syringe to project from the shield in a second direction;

securing the syringe within the shield;

moving the shield containing the syringe to a position for injection of the contents of the syringe;

injecting the contents of the syringe while it is within the shield; and releasing the spent syringe from the shield in a direction away from the direction in which the plunger of the syringe projects, thereby avoiding contamination of the shield from contact with the needle.

28. The method as defined in claim 27 wherein the direction of movement for the removing of the spent syringe from the shield is in the direction in which the needle of the syringe points when the syringe is within the shield.

29. An injection shield for a syringe containing radioactive material, the syringe having a tubular body with a needle mounted upon an opening in a first end of the body and a plunger mounted in an opening in a second end of the body, the second end of the syringe body having a flange thereon the injection shield comprising, a wall portion having opposing side edges and a radiation-dense window mounted therebetween;

a stop mounted on the wall portion, the stop having an arm projecting toward the free edges of the jaws and sized to extend above the flange on the second end of the syringe;

two radiation-dense jaws, each jaw having a far side edge and a near side edge and, the far side edge located away from the wall portion, each jaw pivotally mounted to the wall portion to locate the near side edge of the jaw adjacent to the wall portion and to selectively move the jaw between an open position and a closed position, wherein in the closed position, the free side edges of the jaws abut each other in opposed alignment and cooperate with the wall portion to circumferentially enclose the radioactive material within the body of the syringe, the plunger of the syringe projecting from the shield in a predetermined direction, wherein in the open position, the free side edges of the jaws separate from each other a predetermined distance to allow the syringe to move away from the shield in direction away from the direction in which the syringe plunger is oriented when the jaws are in the closed position;

a finger tab mounted to each jaw; and a spring located between the finger tabs to bias the jaws to the closed position.

* * * * *

UNITED STATES PATENT AND TRADEMARK OFFICE
CERTIFICATE OF CORRECTION

PATENT NO.    : 6,162,198  
DATED         : December 19, 2000  
INVENTOR(S)   : Jack L. Coffey, Steven G. Hauser and Bing Bing Zhu Page 1 of 1

It is certified that error appears in the above-identified patent and that said Letters Patent is hereby corrected as shown below:

<u>Column 10,</u>
Line 38, change "f" to -- of --

<u>Column 12,</u>
Line 44, change "and, the far side" to -- and a finger tab, the far side --

Signed and Sealed this

Fifteenth Day of October, 2002

*Attest:*

*Attesting Officer*

JAMES E. ROGAN
*Director of the United States Patent and Trademark Office*